United States Patent
Zaragoza et al.

(10) Patent No.: US 6,565,012 B1
(45) Date of Patent: May 20, 2003

(54) AIR FRESHENER

(75) Inventors: Robert Zaragoza, Woodmere, NY (US); Thomas Friedrich, New York, NY (US)

(73) Assignee: ZaragozaZaragoza, Inc., New York, NY (US)

( * ) Notice: Subject to any disclaimer, the term of this patent is extended or adjusted under 35 U.S.C. 154(b) by 151 days.

(21) Appl. No.: 09/661,616

(22) Filed: Sep. 14, 2000

Related U.S. Application Data

(63) Continuation-in-part of application No. 09/650,163, filed on Aug. 29, 2000.

(51) Int. Cl.[7] .................................................. A24F 25/00
(52) U.S. Cl. .......................................... 239/44; 237/57
(58) Field of Search ................... 239/44, 57; 220/23.87, 220/23.83, 23.91, 288, 780, 662, 601, 366.1, 367.1, 62.14; 215/43, 321, 317, 382

(56) References Cited

U.S. PATENT DOCUMENTS

| | | | |
|---|---|---|---|
| 1,701,728 A | * | 2/1929 | Phillips |
| 2,383,960 A | | 9/1945 | DuPuy |
| 2,456,244 A | | 12/1948 | Bash |
| 3,123,303 A | * | 3/1964 | Dearling |
| 3,962,824 A | | 6/1976 | Poston |
| 4,165,835 A | | 8/1979 | Dearling |
| 4,206,842 A | * | 6/1980 | Burridge, Jr. |
| 4,477,414 A | | 10/1984 | Muramoto et al. |
| 4,525,950 A | | 7/1985 | Glassman |
| D288,842 S | | 3/1987 | Kwiatkowski |
| 4,708,851 A | | 11/1987 | Freytag von Loringhoven |
| 4,732,321 A | | 3/1988 | Dolan |
| 4,874,107 A | * | 10/1989 | Arnau-Munoz et al. |
| 4,928,881 A | | 5/1990 | Barlics et al. |
| 5,000,383 A | * | 3/1991 | van der Heijden |
| 5,230,867 A | | 7/1993 | Kunze et al. |
| 5,353,546 A | | 10/1994 | Bock |
| 5,544,812 A | * | 8/1996 | Torres |
| 5,894,948 A | * | 4/1999 | Yeh |
| D412,569 S | | 8/1999 | Muller |

\* cited by examiner

Primary Examiner—Christopher Kim
(74) Attorney, Agent, or Firm—Bazerman & Drangel, PC

(57) ABSTRACT

An air freshener dispenser having a transparent outer container. A detachably mounted top has one or more openings to allow circulation. A detachable insert is suspended in the outer container and thus floats in the outer container above the outer container's bottom. Additional decorative elements may be positioned between the outer container and the insert. An intermediate decorative insert can be removably positioned between the outer container and the transparent or translucent insert.

10 Claims, 8 Drawing Sheets

AIR FRESHENER

BACKGROUND OF THE INVENTION

This application is a continuation-in-part of application Ser. No 09/650,163, filed Aug. 29, 2000, presently pending.

FIELD OF THE INVENTION

The present invention relates generally to air freshener dispensers, more particularly, an air freshener container with multiple replaceable decorative inserts for holding and dispersing a scented liquid by means of a wick.

PRIOR ART

Since almost the beginning of civilization man has used various means to improve his environment by dispersing fragrances to the atmosphere. He has burned incense, sprayed perfumes and evaporation scented liquids. With regard to the latter, it is well known to disperse liquid perfume mixtures by a wick partially immersed in a scented liquid.

Attempts have been made to improve the appearance of such scented liquid systems by the use of a decorative outer container. For example, U.S. Pat. No. 4,928,881 issued to John J. Barlics and Glen D. Barlics on May 29, 1990, discloses an air freshener having a base holding a scented liquid, a wick extending from the base, and a decorative opaque shroud or cover surrounding the wick in the form of flower petals which hides the wick. While the scented fluid may be replaced in the base, allowing the fragrance to be changed, the appearance of the air freshener is static. There is no visual indication of a change in the scented liquid. Equally, its construction inherently gives an inexpensive, plastic appearance inappropriate to many environments.

Similarly, U.S. Pat. No. 2,456,244, issued on Sep. 7, 1946, U.S. Pat. No. 4,165,835, issued on Aug. 28, 1979, U.S. Pat. No. 5,353,546 issued on Oct. 11, 1994 disclose various opaque containers for air fresheners. Each offers no opportunity to modify the appearance of the container or to give a visual clue as to the liquid being dispersed.

BRIEF SUMMARY OF THE INVENTION

The present invention is an air freshener dispenser which allows a person to easily change both the fragrance dispersed and the appearance of the air freshener. The air freshener dispenser has an outer container which is at least in part transparent or translucent. The outer container may have a complex shape or a design on its surface for decorative purposes, if desired. A top is detachably mounted on the outer container. The top has one or more openings to allow circulation of air between the atmosphere and the interior of the outer container. A scented liquid is contained in a transparent or translucent insert detachably mounted in the outer container. The insert is suspended from the top of the outer container, and thus can be designed to appear to float in the outer container above the outer container's bottom.

The insert would be visible through the walls of the transparent or translucent outer container. The insert may be of any other suitable shape, it may be transparent or translucent. The variations in the inserts shape and color of the fluid it contains allows each insert to make a different decorative impression for the air freshener as a whole. Since both its shape and color can be varied to correspond to the scent contained in it, it may be used to act as a visual clue to the contained scent and the amount of fluid remaining. In addition, decorative elements may be positioned between the outer container and the insert.

If desired, an intermediate transparent or translucent insert can be positioned between the outer container and the insert so as to immediately surround the insert. The intermediate insert would have molded into it or on its surface various decorative elements. Such intermediate insert is removable to allow substitution of alternate intermediate inserts with different decorative affects. Aside from the decorative function, the intermediate insert effectively acts to reduce breakage by giving extra support during shipping storage and display.

The intermediate insert also acts to form a dead air space as insulation for maintaining the insert at a desired temperature. To protect fragrances which change upon exposure to ultraviolet light, the intermediate insert can be made from a material which acts as an ultraviolet filter. Similarly, the intermediate insert can be made of a polarizing material for special effects.

DETAILED DESCRIPTION OF THE PREFERRED EMBODIMENTS

Figure 1:
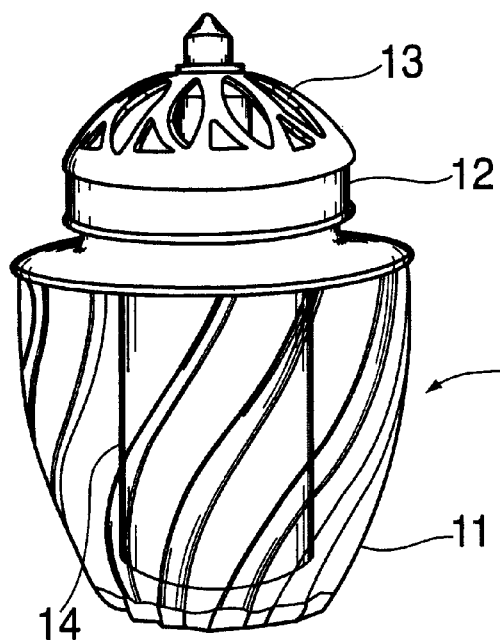
FIG. 1 is a perspective view of an air freshener in accordance with the present invention.
Figure 3A:
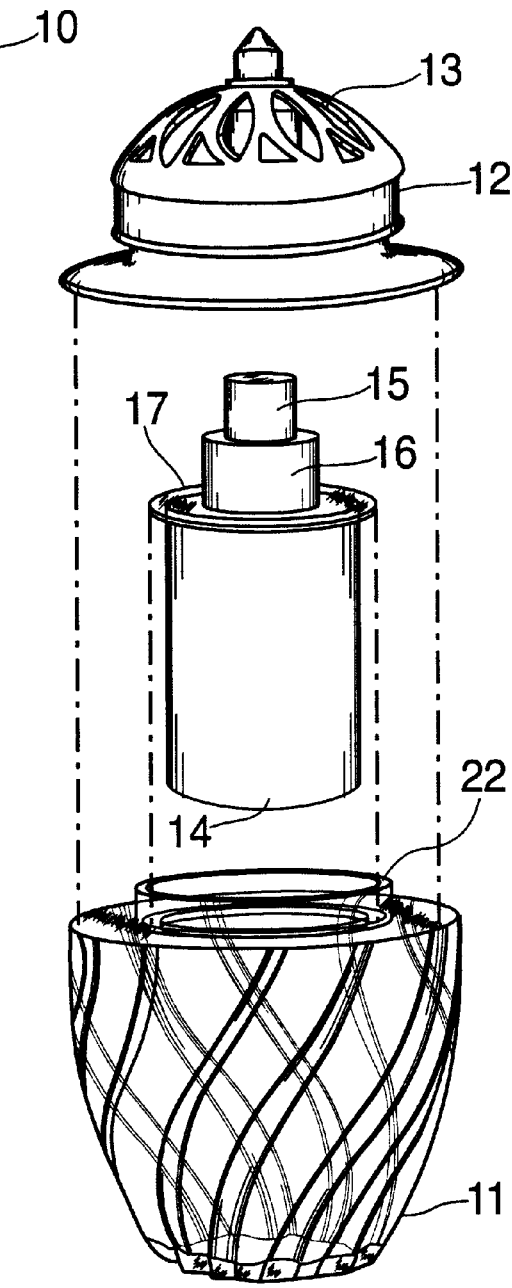
FIGS. 3a–3c are exploded perspective views of the present invention having different shaped inserts.

Referring to FIGS. 1, 2 and 3a–3c, an air freshener 10 is formed from a transparent or translucent container 11 with a top 12 having openings 13. Detachably mounted within container 11 is insert 14 which containing a scented fluid. The insert 14 has a wick 15 one end of which is immersed in the fluid contained in insert 14 and the other end which extends beyond a guide 16 at the top of insert 14.

Figure 2:
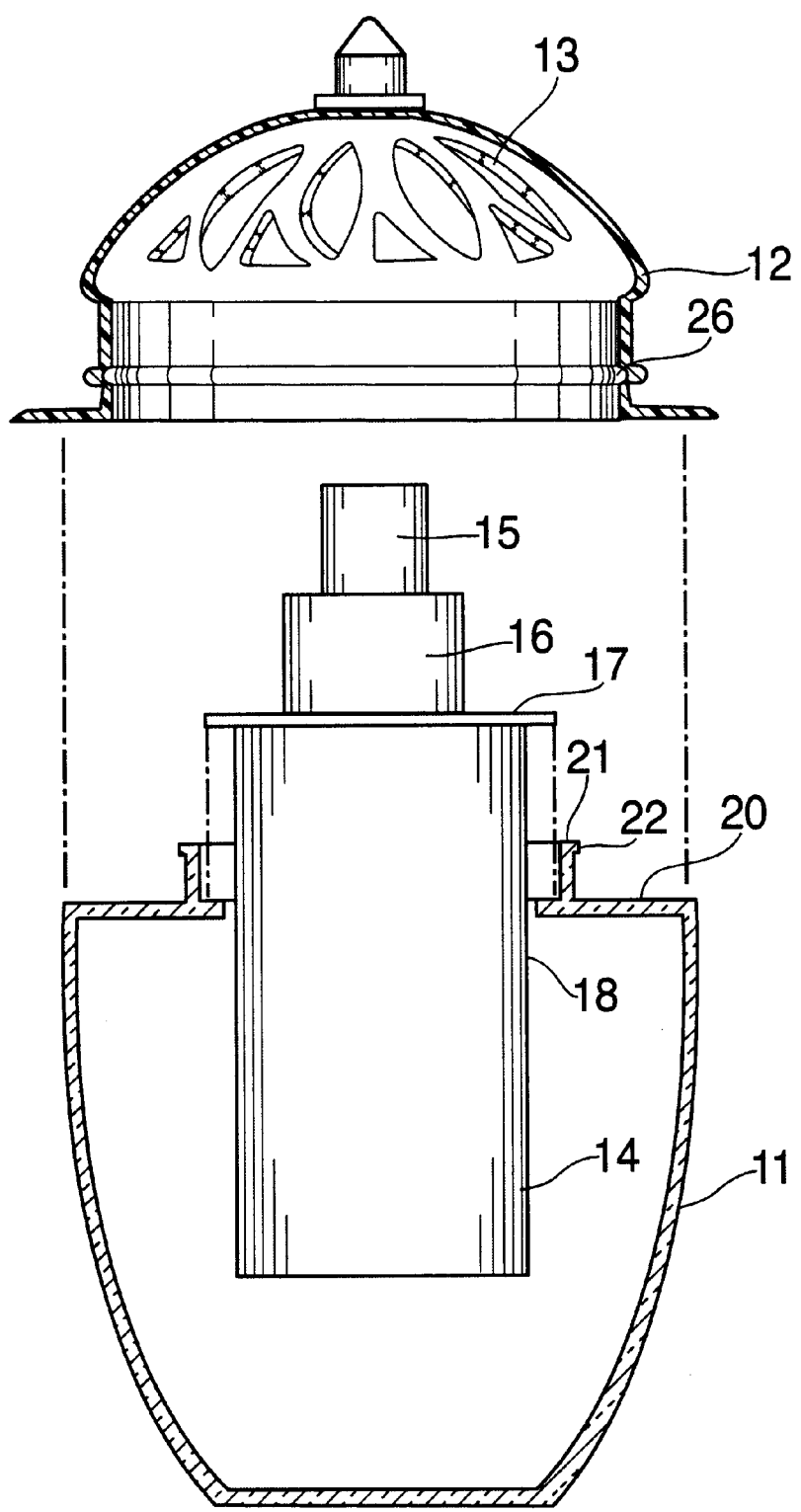
FIG. 2 is an exploded, cut away, side view of the air freshener of the present invention.

As seen most clearly in FIG. 2, container 11 has the top portion 20 with an opening 18 to allow mounting of the insert 14. Surrounding and set back from the opening 18 is cylindrical member 21 having a lip 22. Insert 14 has a mounting disc 17 at one end of a size to fit within cylinder 21 but larger than opening 18. Thus, disc 17 acts as a support for suspending insert 14 in cylinder 11. This allows cylinder 14 to be suspended above the bottom 25 of container 11 when the apparatus is closed. Lip 22 interacts with a groove 26 in top 12 to hold top 12 in place. The fit between lip 22 and groove 26 is such as to hold the top 12 in place but allow its removal when pressure is applied to top 12.

Figure 3B:
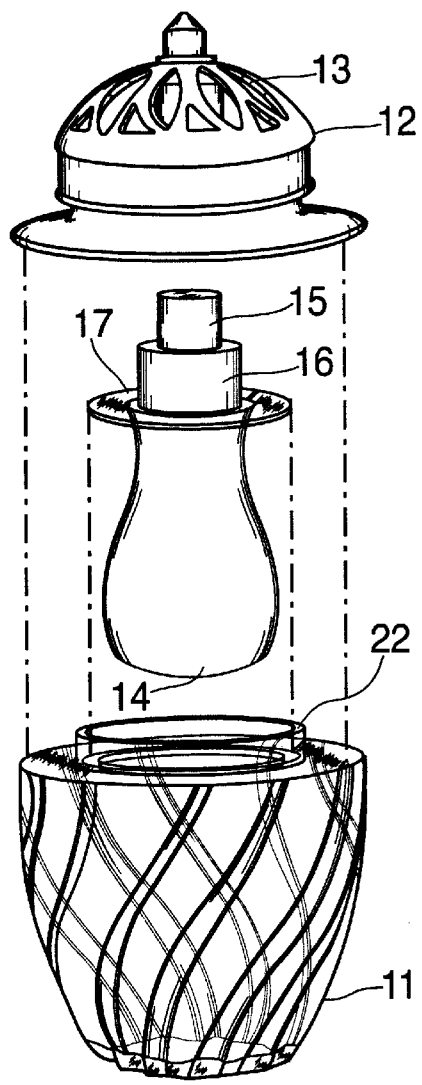
Figure 3C:
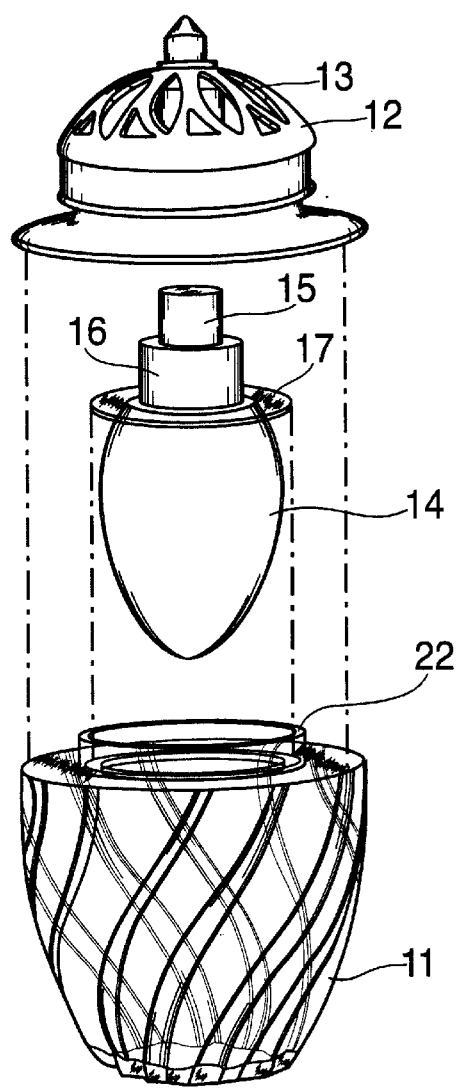
Figure 4C:
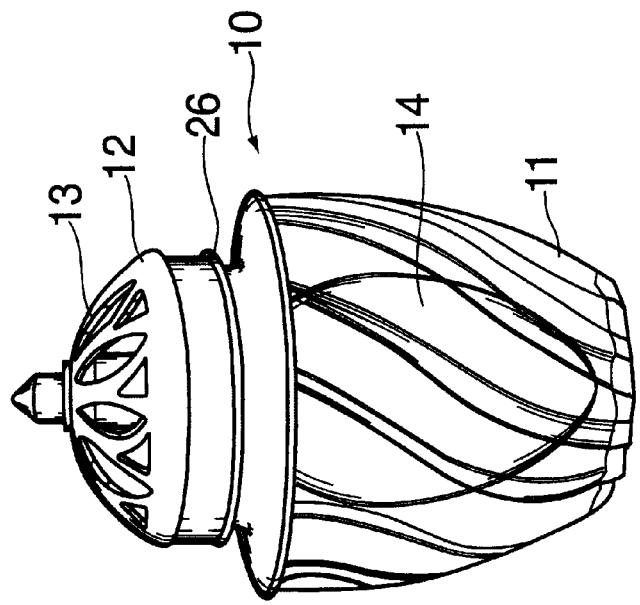
FIGS. 4a–4c are perspective views of the air freshener of the present invention with different inserts.
Figure 4B:
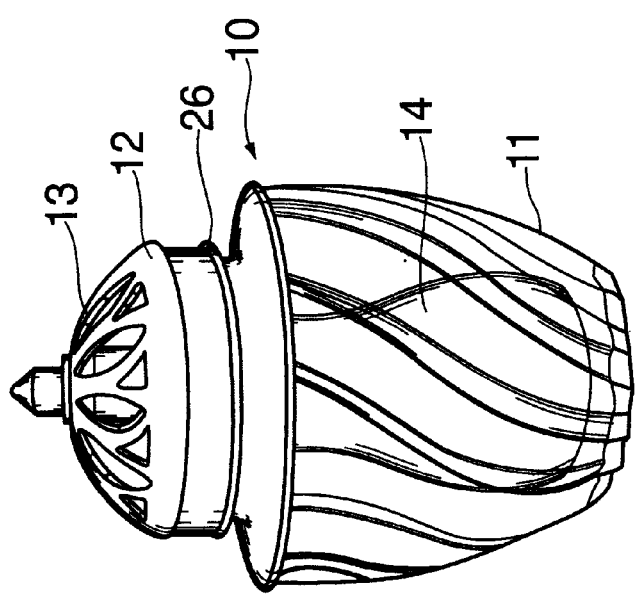
Figure 4A:
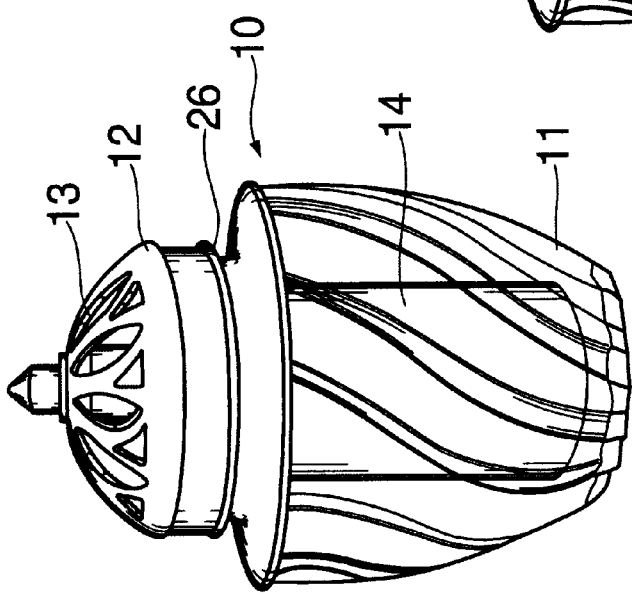
Figure 5:
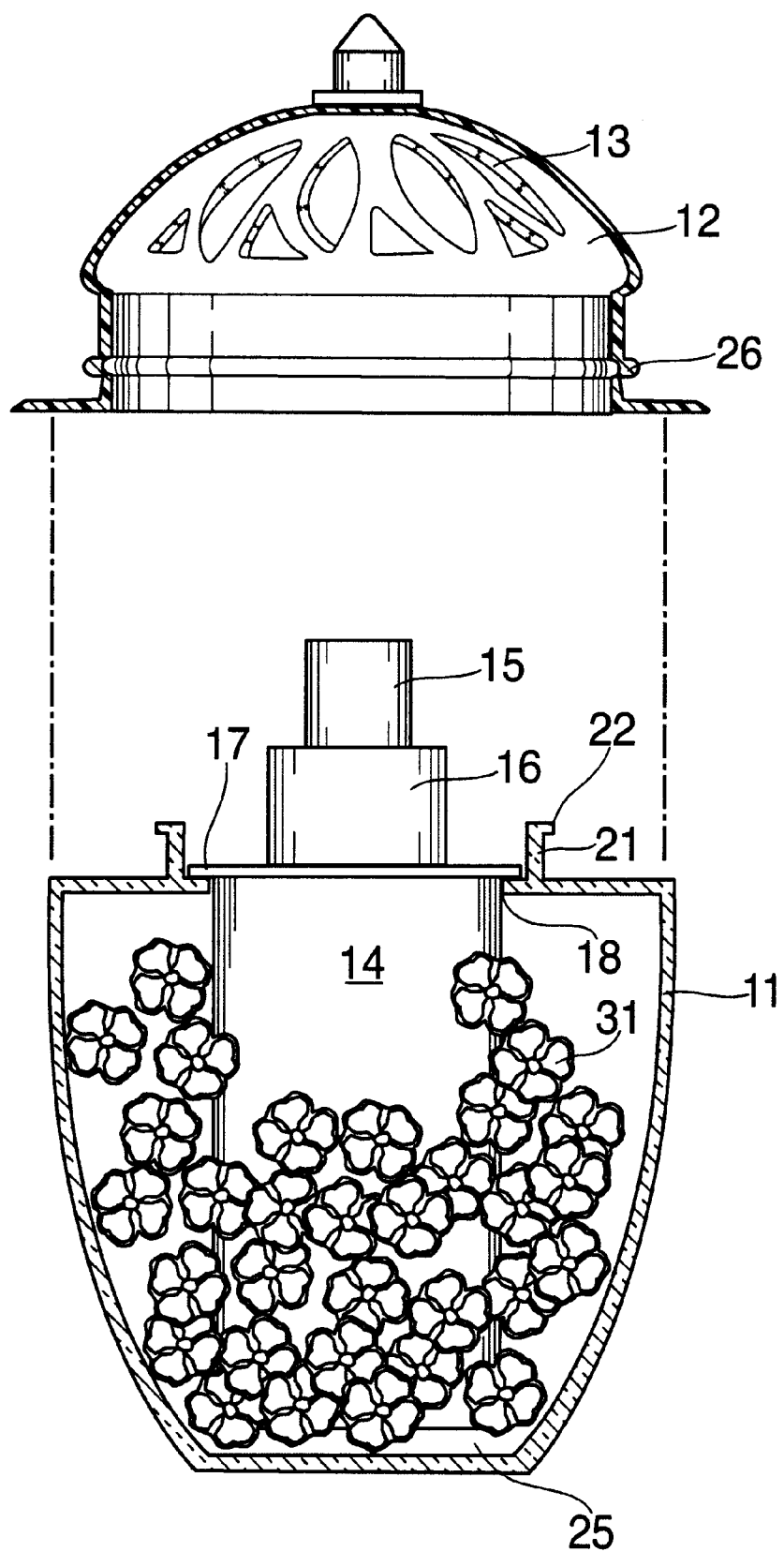
FIG. 5 is an exploded, cut away, side view of the air freshener of FIG. 1 in which decorative elements such as flowers have been inserted in the body of the air freshener.

FIGS. 3b and 3c are exploded views of the container of the present invention with different shaped inserts 14. FIGS. 1, 4a–c show the completed air freshener 10 of the present invention with different shaped inserts 14. As seen in FIG. 5, the space formed between insert 14 and outer container 11, decorative elements, such as botanicals, may be inserted to form a decorative image. The botanicals may be sufficiently loosely packed or transparent so that the insert 14 may be viewed through the outer container 11. Alternatively, the decorative elements 31 may be sufficiently packed and opaque such as to obscure the view of the insert 14.

Figure 6:
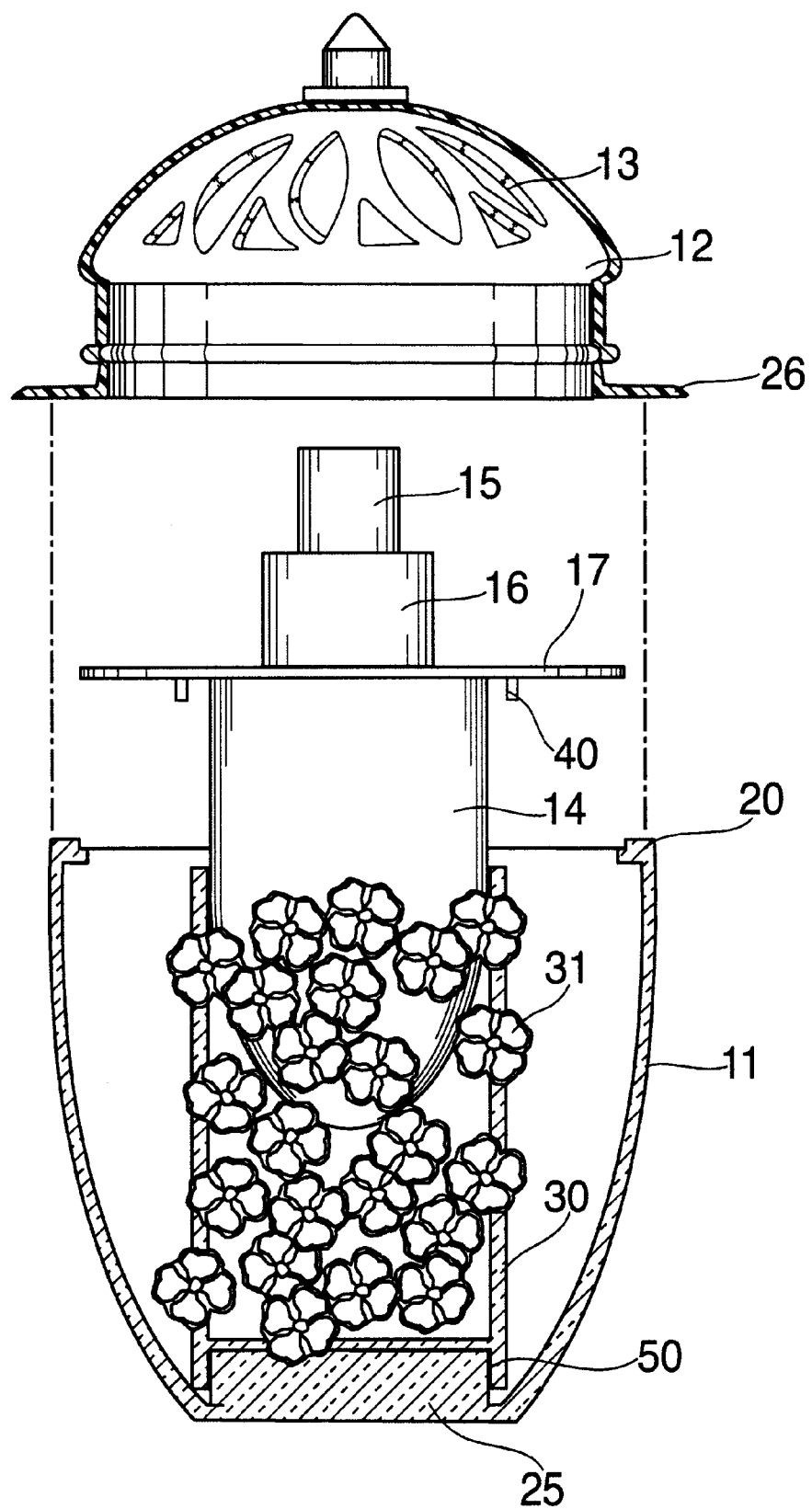
FIG. 6 is an exploded, cut away, side view of an alternate embodiment of the present invention in which there is an intermediary insert having decorative elements attached to an intermediate insert.

As can be seen in FIG. 6, another embodiment of the present invention adds an additional intermediary insert 30 between insert 14 and outer container 11. This intermediate insert 30 is in the form of a translucent or transparent cylinder and is of sufficient length to extend from top 20 of the outer container 11 to the bottom of the container 11 with the top of intermediate insert 30 flush with the top 20 of the outer container 11. It is in frictional engagement with a circular circumferential ridge 40 on mounting disk 17. The bottom of intermediate insert 30 is held in place by a conventional means such as frictional or snap-in engagement with a cylinder 50 mounted on the bottom 25 of container 11. Thus, it is held in place both by mounting disk 17 and cylinder 50 of outer container 11, giving support to the structure. The intermediate insert 30 should be made of a transparent or translucent material and have either embedded in its structure or cemented to its surfaces decorative elements such as botanicals, including berries, slices of fruit, leaves, seeds, flowers, sprigs, branchlets and Queen Anne's lace. When the insert 14 and the top 20 are removed, the intermediate insert 30 may be pulled from the container and replaced with an alternate cylinder to allow a change in decoration or decorative effect.

The intermediate insert 30 not only allows for the addition of alternate decorative elements but also gives support to the entire air freshener 10. Further, it acts to confine and insulate the insert 14, thus, allowing insert 14 to be maintained at a constant temperature. Additional visual effects may be obtained by making the cylinder from a polarized element or having polarized sections in it. Such polarized section can be worked with polarized elements in the insert 14 to produce various visual effects. Finally, intermediate insert 30 may be made of a material to act as an ultraviolet filter to protect the fluid.

Figure 7:
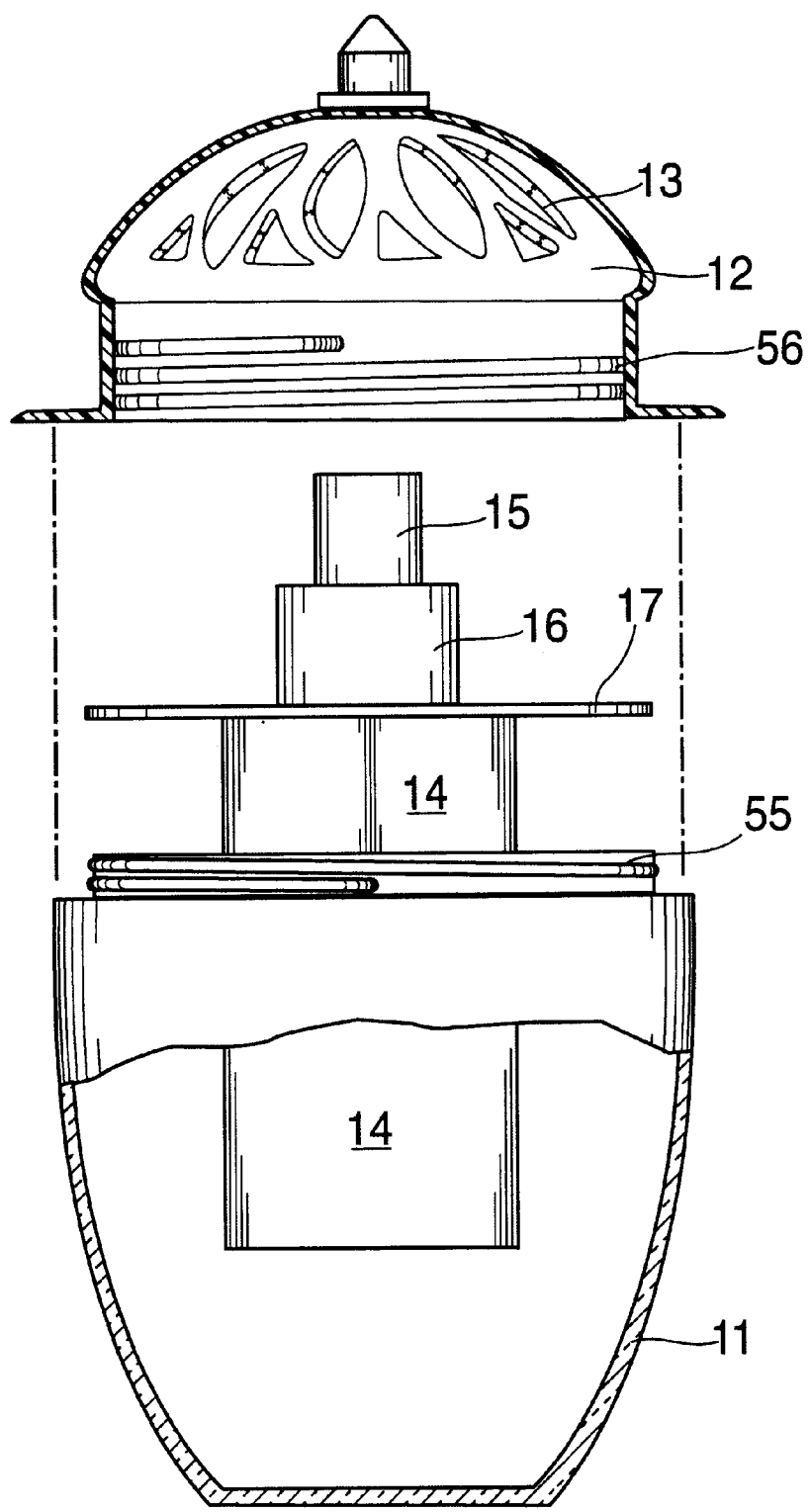
FIG. 7 is an exploded, partially cut away, side view of another embodiment of the present invention in which the cap is attached to the outer container by means of a screw thread.
Figure 8:
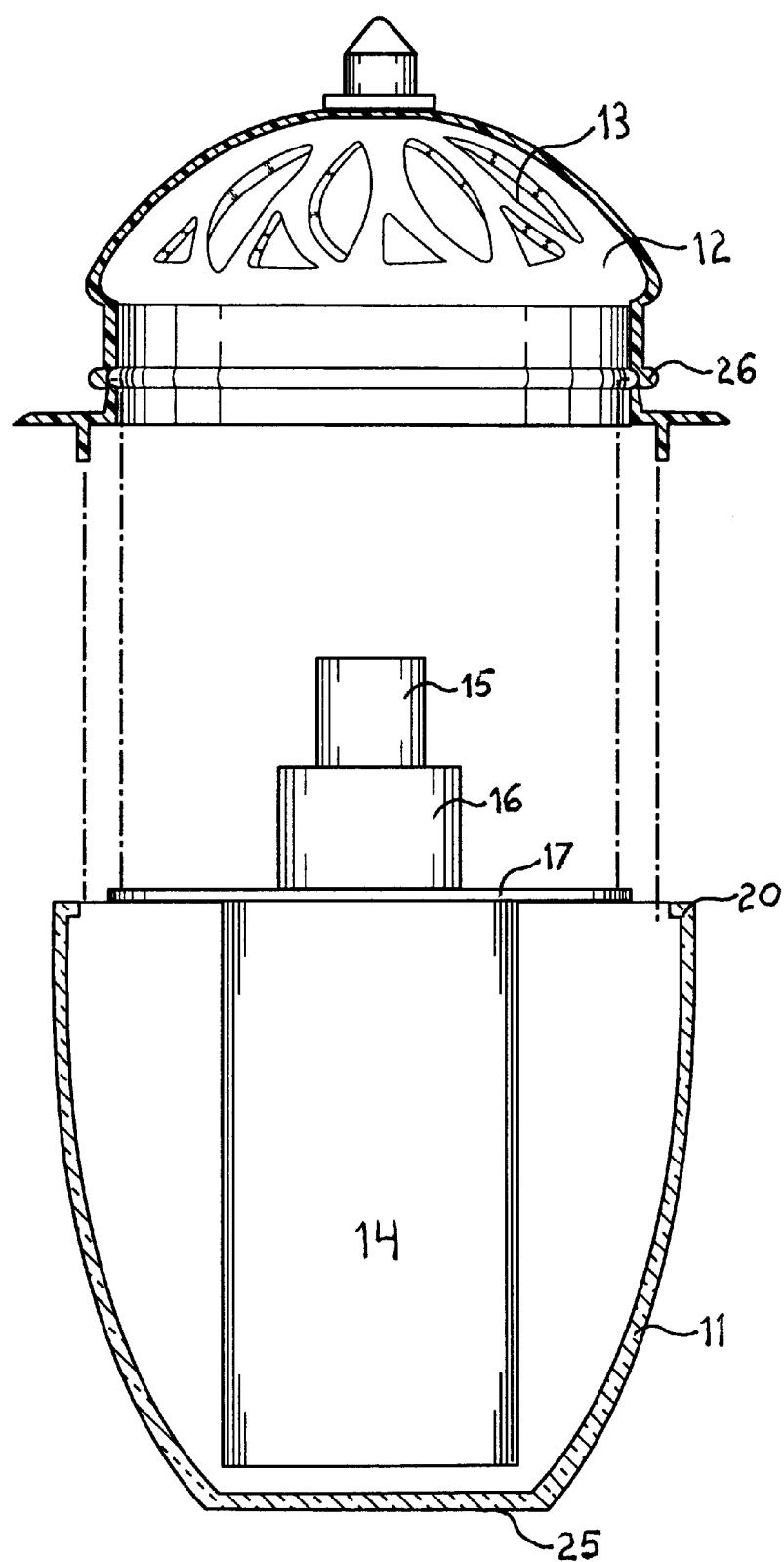
FIG. 8 is an exploded, cut away, side view of an alternative embodiment of the air freshener of FIG. 1 in which the insert is held in place by a snap attachment to the cap.

FIG. 7 shows an air freshener where the cap 12 is held in place by screw threads on 55 and 56. FIG. 8 discloses an alternate embodiment of the invention in which the support flange 17 snaps into groove 26 to hold insert 14 in place in outer container 11.

While the invention has been described as having a preferred design, it is understood that it is capable of further modification, uses and/or adaptations of the invention following in general principle of the invention and including such departures from the present disclosure as come within known or customary practice in the art to which the invention pertains, as may be applied to the central figures hereinabove set forth and fall within the scope of the invention of the limits of the appended claims.

We claim:

1. An air freshener system comprising:

a first, hollow receptacle with an opening at one end;

a cap having openings therein positioned over the opening in said first hollow receptacle;

a second receptacle located partially within said first receptacle and partially within said cap, for containing a scented liquid and having a wick partially positioned in said second receptacle;

said second receptacle having a rim which is larger than the opening in said first receptacle so as to mechanically support said second receptacle in said first receptacle;

the rim of said second receptacle and the cap being of such size and shape so as to hold the second receptacle in place in the first receptacle while exposing the wick to the atmosphere through the openings in the cap.

2. The air freshener of claim 1 wherein the first hollow receptacle is formed from a transparent or translucent material.

3. The air freshener of claim 1 wherein the second receptacle is formed from a transparent or translucent material.

4. The air freshener of claim 1 wherein the first hollow receptacle has a cylindrical retaining wall around the opening in which the rim of the second receptacle is held in position.

5. The air freshener of claim 4 wherein there are screw threads on the cap and on the cylindrical retaining wall on the first hollow receptacle whereby the cap is held in place on the first hollow receptacle.

6. The air freshener of claim 1 wherein ornamental objects are positioned between the first hollow receptacle and the second receptacle.

7. The air freshener of claim 1 wherein a detachable insert is positioned between the first hollow receptacle and the second receptacle.

8. The air freshener of claim 7 wherein ornaments are attached to the detachable insert.

9. The air freshener of claim 7 wherein said detachable insert is constructed of a UV filtering material.

10. The air freshener of claim 7 where in said detachable insert is positioned between said first hollow receptacle and said second receptacle in a manner to support said cap.

\* \* \* \* \*